United States Patent [19]

Whalon et al.

[11] Patent Number: 5,716,831
[45] Date of Patent: Feb. 10, 1998

[54] METHOD AND TEST KIT FOR DETECTING INSECTICIDE RESISTANCE

[75] Inventors: Mark E. Whalon, East Lansing, Mich.; Joel M. Wierenga, Langhorne, Pa.

[73] Assignee: Board of Trustees operating Michigan State University, East Lansing, Mich.

[21] Appl. No.: 449,561

[22] Filed: May 24, 1995

[51] Int. Cl.[6] .............................. C12Q 1/44; C12Q 1/34; G01N 33/53

[52] U.S. Cl. .................... 435/19; 435/18; 435/4; 435/970; 435/975

[58] Field of Search ................... 435/19, 18, 4, 435/975, 970

[56] References Cited

U.S. PATENT DOCUMENTS

| | | | |
|---|---|---|---|
| 2,292,450 | 8/1942 | Kohn | 435/19 |
| 3,785,930 | 1/1974 | Ellis | 435/19 |
| 3,843,452 | 10/1974 | Freake et al. | 435/19 |
| 4,055,394 | 10/1977 | Friedman et al. | 435/19 |
| 4,225,557 | 9/1980 | Hartl et al. | 435/19 |
| 4,368,272 | 1/1983 | Kashket | 435/19 |
| 4,476,226 | 10/1984 | Hansen et al. | 435/19 |
| 4,540,659 | 9/1985 | Litman et al. | 435/19 |
| 4,582,795 | 4/1986 | Shibuya et al. | 435/19 |
| 4,673,638 | 6/1987 | Grosch et al. | 435/19 |
| 4,696,674 | 9/1987 | Cipar | 435/19 |
| 4,713,344 | 12/1987 | Markhart | 435/19 |
| 4,789,629 | 12/1988 | Baker et al. | 435/19 |
| 4,826,759 | 5/1989 | Guire et al. | 435/19 |
| 4,826,772 | 5/1989 | Meathrel | 435/19 |
| 4,839,297 | 6/1989 | Freitag | 435/19 |
| 4,963,325 | 10/1990 | Lennon | 435/19 |
| 5,015,572 | 5/1991 | Backhaus et al. | 435/19 |
| 5,223,405 | 6/1993 | Howell et al. | 435/19 |
| 5,352,451 | 10/1994 | Miller et al. | 435/19 |
| 5,358,934 | 10/1994 | Borovsky et al. | 435/19 |

OTHER PUBLICATIONS

Chang et al, Pesticide Biochemistry and Physiology 27, 30–35 (1987) Month not available (Please print).

Dary et al (J. Econ. Entomol. 83 2187–2192 (1990) Month not availabe (Please print).

Devonshire, A., et al., Bulletin of Entomological Research 82 459–463 (1992) Month not available (Please print).

O'Hara, D., et al., Great Lakes Vegetable Growers (Abstract Jan. 1993) Month not available (please print).

(List continued on next page.)

Primary Examiner—Louise Leary
Attorney, Agent, or Firm—Ian C. McLeod

[57] ABSTRACT

A method and test kit for determining insect resistance based upon an esterase in the body fluid of the insect in the field. The method and kit includes an absorbent material pad (12) containing a dry substrate for the esterase which is preferably mounted on a fluid impermeable sheet (11). A roller (20) is preferably used to express the fluids from the insect onto the pad 12. The fluids are sufficient to enable the esterase to react with the substrate to produce an intermediate compound which is reacted with a chromogen to produce a visually detectable image with an intensity which varies directly as a function of the amount of the esterase and which is easily determinable by the farmer. The method and kit is particularly useful with homopteran, particularly aphids which are a problem in potatoes.

17 Claims, 1 Drawing Sheet

OTHER PUBLICATIONS

Pasteur, N., et al., Mosquito News 41 181–183 (1981) Month not available (Please print).

Rees et al (J. Am. Mosq. Control Assoc. 1 23–27 (1985) Month not available. (Please print).

Marullo, R., et al., J. Appl. Ent. 106 212–214 (1988) Month not available (Please print).

Pasteur et al, Journal of Economic Entomology 82 347–353 (1989) Month not available. (Please print).

Bisset et al, Bulletin of Entomological Research 80 245–250 (1990) Month not available, (Please print).

Halliday, W., et al. (J. Med. Entomol. 22 574–576 (1985) Month not available. (Please print).

El–Khatib, Z., et al (J. of Economic Entomology 78 1023–1029 (1985) Month not available. (Please print).

Huang, T., et al., Pharmaceutical Research 10 639–648 (1993) Month not available. (Please print).

Devonshire, A.L., et al., Pestic. Biochem. & Physiol. 18 235–246 (1982) Month not available. (Please print).

Field et al., Biochem. J. 251 309–312 (1988) Month not available. (Please print).

Moores et al., Pestic. Sci. 26 324–329 (1989) Month not available. (Please print).

Devonshire & Sawicki, Nature 280 140–141 (1979) Month not available (Please print).

O'Hara, M.S. Thesis, Michigan State Unviersity (1992) Month not available (Please print).

Abdel–Aal, Y.A.I., et al., Pestic. Biochem. & Physiol. 38 255–266 (1990) Month not available. (Please print).

Bush, M.R., et al., J. Econ. Entomol. 86 213–225 (1993) Month not available (Please print).

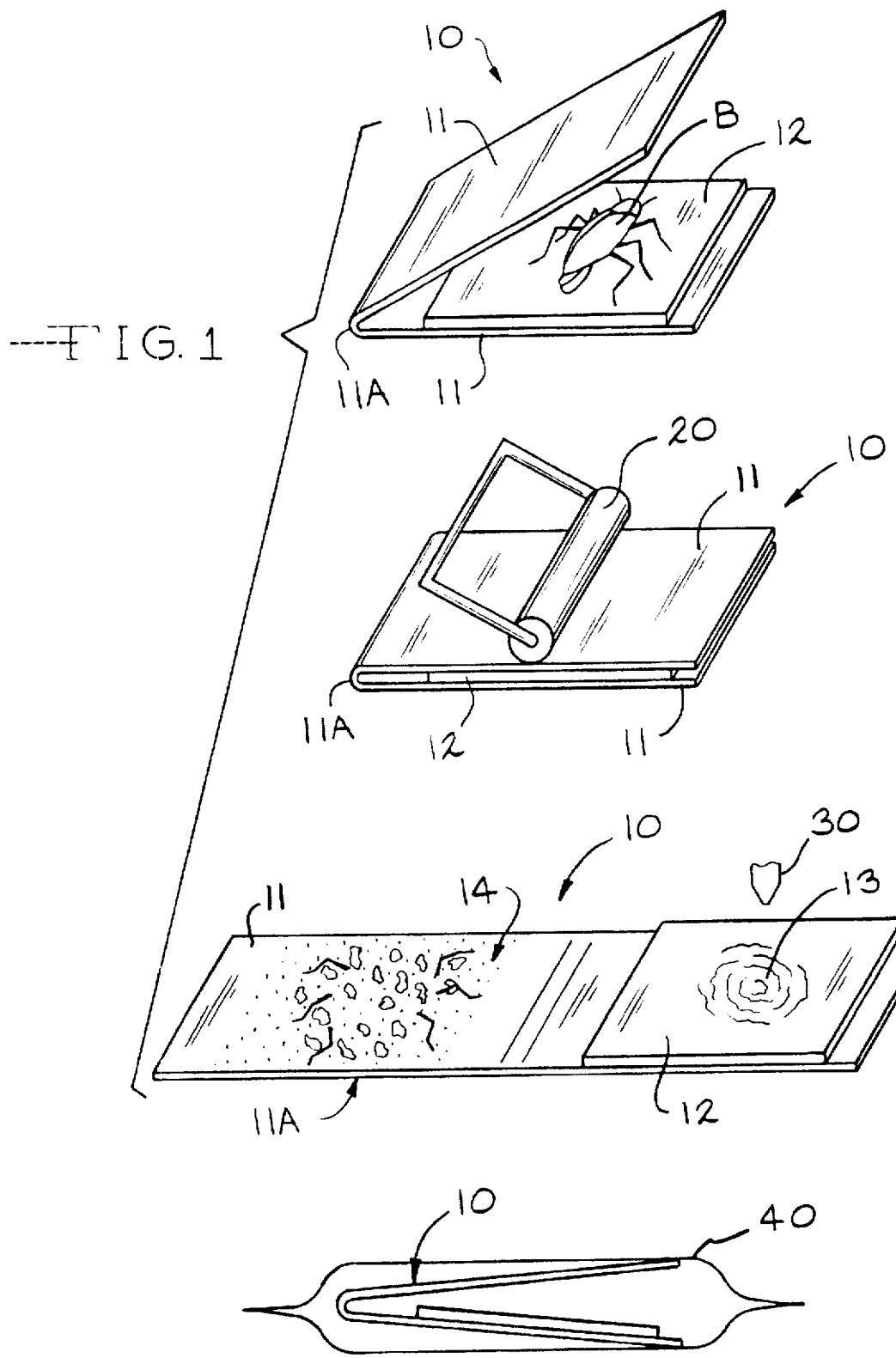

METHOD AND TEST KIT FOR DETECTING INSECTICIDE RESISTANCE

BACKGROUND OF THE INVENTION

(1) Field of the Invention

The present invention relates to an assay method and test kit for detecting insect esterases which cause insecticide resistance. In particular, the present invention relates to a method wherein a dried substrate for the esterases is provided in an absorbent material and wherein the whole insect is crushed on the absorbent material to release body fluid containing the esterases. The esterases in the fluid react with the substrate in the absorbent material to produce an intermediate compound. A chromogen in solution is then added to the absorbent material to provide a visually detectable image. The color of the image is a direct function of the amount of the esterases in the insect and thus the insect resistance of the particular insect. The results with a few insects (one or more) correlates well with the population in a particular field for a crop plant.

(2) Description of Related Art

The prior art has recognized a need for a reliable assay method for identifying insects which are resistant to esterase degradable insecticides such as organophosphates and pyrethoids and have developed sophisticated assays for detecting esterase levels. Thus Chang et al (Pesticide Biochemistry and Physiology 27, 30–35 (1987)); Dary et al (J. Econ. Entomol. 83 2187–2192 (1990)) and Devonshire, A., et al. (Bulletin of Entomological Research 82 459–463 (1992)) describe the use of an immunoassay and/or an electrophoresis assay for this purpose. For the Chang et al assays, a large number of the insects at a single stage of development are crushed, homogenized, and mixed with a buffer, which is optional for the immunoassay. The immunoassay is conducted with an antibody coated on microplate wells and naphthyl acetate is used as a substrate for detection. This assay is reliable but cannot easily be performed by the farmer in the field. Also described is a microassay using electrophoresis. The naphthyl acetate and Fast Blue RR salt as a chromogen are used after the electrophoresis. This assay is also difficult for the farmer to perform in the field. The microassay results were variable. The immunoassay results were reliable. The other references describe similar assays.

O'Hara, D., et al, Great Lakes Vegetable Growers (Abstract January 1993) describes similar assays plus an insecticide slide dip assay. This latter assay attempts to measure the affect of the esterase on the insecticide directly. A similar type of direct assay is described by Chang, C., et al. (Pesticide Biochemistry and Physiology 27 30–35 (1987)) using thin layer chromatography or electrophoresis with radioactive insecticides. Homogenates of large numbers of insects were used in these assays.

Pasteur, N., et al., Mosquito News 41 181–183 (1981)) describe a filter paper assay for detecting organophosphate insecticide resistance. In this assay, filter paper is blotted with a homogenate of a single mosquito using the bottom of a hemolysis tube. This procedure is repeated 10 to 20 times with insects and then the filter paper is immersed in buffer containing α-naphthyl acetate as the substrate. A "fixing" solution (10% acetic acid) stops the action of the enzyme. The paper is then "stained" with Fast Garnett GBC salt dye as a chromogen. The intensity of the response is correlated to the esterase activity of the insects. This test is also not easily adapted to field conditions for use by the farmer. Rees et al (J. Am. Mosq. Control Assoc. 1 23–27 (1985)) describes a similar assay method using naphthyl acetate with Fast Red TR dye as a staining agent or chromogen. Marullo, R., et al (J. Appl. Ent. 106 212–214 (1988)) describe a similar assay with α-naphthyl acetate and Fast Garnett as a dye. A number of insects are used in these assays as well. Pasteur et al (Journal of Economic Entomology 82 347–353 (1989)) describe an improvement on the earlier assay, using Triton X-100 (a surfactant), wherein the mosquito is aspirated through the filter paper to eliminate body parts. In an alternative procedure air dried filters containing α-naphthyl acetate are stored in plastic bags. Bisset et al (Bulletin of Entomological Research 80 245–250 (1990)) describe an assay in the manner of Pasteur, N. et al (Mosquito News, 181–183 (1981)). Halliday, W., et al (J. Med. Entomol. 22 572–576 (1985)) describe the use of the filter paper test for genetic work. El-Khatib, Z., et al (J. of Economic Entomology 78 1023–1029 (1985)) also describe the use of the Pasteur, N. et al assay in comparing the insect resistance of mosquitoes.

The patent arts have described various assays for microorganisms and for animal and human conditions using an absorbent material containing reagents. Many of these assays use devices which press two components together to react chemicals. Illustrative of the prior art are U.S. Pat. Nos. 2,292,450 to Kohn; 3,785,930 to Ellis; 3,843,452 to Freake et al; 4,055,394 to Friedman et al; 4,368,272 to Kashket; 4,225,557 to Hartl, et al; 4,476,226 to Hansen et al; 4,540, 659 to Litman et al; 4,582,795 to Shibuya et al; 4,673,638 to Grosch et al; 4,789,629 to Baker et al; 4,826,759 to Guire et al; 4,826,772 to Meathrel; 4,839,297 to Freitag, K; 4,963, 325 to Lennon; 5,015,572 to Backhaus et al. In none of these assays was there any description of field assays for insects.

U.S. Pat. No. 4,713,344 to Markhart describes a press for removing all liquids from tissue. Usually the prior art uses some means for the extraction of the analyte from the tissue. U.S. Pat. No. 5,223,405 to Howell et al describes a device where in vivo tissue is pressed by the device to release fluids (sap) into an absorbent material layer. The liquid impregnated in the tissue is then tested in the laboratory.

There is a need for a simple and reliable test for esterases in insects which can be used in the field by the farmer.

OBJECTS

It is therefore an object of the present invention to provide an assay method and test kit which can be easily used in the field without the need for any laboratory procedures. Further, it is an object of the present invention to provide a test kit which is inexpensive to construct and simple to use. These and other objects will become increasingly apparent by reference to the following description and the drawings.

DESCRIPTION OF DRAWINGS

FIG. 1 is a schematic perspective view of Steps 1 to 3 in the method of the present invention for using the test kit, including a test device 10 and a roller 20.

FIG. 2 is a front cross-sectional view of the device 10 in a container 40.

DESCRIPTION OF PREFERRED EMBODIMENTS

The present invention relates to a method for detecting insect resistance to insecticides caused by an esterase produced by the insect which comprises: providing an absorbent pad containing a dry substrate for the esterase which reacts to produce an intermediate compound and reacts with a chromogen to provide a visually detectable image; crushing a single whole insect against the pad so that the esterase is released in the body fluid of the insect which reacts with the substrate to produce the intermediate compound; reacting the intermediate compound with the chromogen; and determining an intensity of an image produced on the pad by the reaction of the esterase with the substrate and the intermediate compound with the chromogen, wherein the intensity of the image varies directly as a function of an amount of the esterase in the insect.

Further the present invention relates to a kit for detecting insect resistance to insecticides caused by an esterase produced by the insect which comprises: an absorbent pad containing a dry substrate for the esterase which reacts with the enzyme to produce an intermediate compound which reacts with a chromogen to produce a visually detectable image on the pad; press means for crushing the whole insect on the pad to release the esterase in body fluids of the insect which reacts with the substrate to produce the intermediate compound which reacts with the chromogen; and a dry chromogen which can be dissolved in water just prior to use, wherein an intensity of the image on the pad varies directly as a function of an amount of the esterase in the insect.

It has unexpectedly been found that the body fluids from a single insect can be used in the method and test kit of the present invention. Since the fluids limit the reaction by providing a definite amount of esterase, there is no need for a stopping agent as used by the prior art. As a result the assay is easily used by the farmer.

In the preferred assay, the body fluid containing the esterase is squeezed or pressed from the insect and reacts with a naphthyl acetate as a substrate to produce an intermediate compound which is naphthol. This compound is then reacted with a chromogen or dye to produce a visually detectable image. It has been found that there is sufficient liquid in the insects to allow the reaction to proceed. This is particularly true of homopteran insects, such as aphids.

Various substrates can be used for carboxyl esterases as described by Huang, T., et al (Pharmaceutical Research 10 639–648 (1993)). Thus carbonates, thiocarbonates, carbamates and esters of naphthol (alpha and beta) and nitrophenol can be used as substrates. Other aromatic compound esterase substrates are known to those skilled in the art. The substrates are applied in a non-aqueous organic solvent which dries readily such as acetone.

The chromogen or dye which is used includes tetrazotized o-diamisidine naphthamidizo blue B (Diazo Blue)which is preferred. Numerous other dyes (Fast Garnett, Fast Red and the like) are well known to those skilled in the art and can be used.

As shown in FIG. 1, the device 10 is preferably includes a folded water impermeable sheet 11 with a fold line 11A. An absorbent material pad 12 is mounted adjacent to one end of the sheet 11 such as by glue or the like. The pad 12 is impregnated with the substrate and the dye and is dry. In use, an insect B is placed on the pad 12 in Step 1. In Step 2, a roller 20 (or other pressing means) for pressing the sheet 11 onto the pad 12 is used to squeeze the insect B to release the fluids including esterases. In Step 3, the sheet 11 is opened so that the pad 12 is exposed and the dye is applied by applicator 30. The intensity of color of the spot 13 is used to measure the amount of esterase in the insect B which is correlated with the insecticide resistance. The device 10 is stored in a sealed container 40 prior to use as shown in FIG. 2. After Step 2, the solid body parts of the insect B are generally removed. An adhesive 14 can be applied to the sheet 11 to aid in removal of the body parts.

The following are non-limiting Examples of the method and test kit of the present invention.

EXAMPLE 1

Fifty (50) insecticide resistance monitoring kits were constructed to use to detect esterase-mediated resistance in green peach aphid (*Myzus persicae* Sulzer). Green peach aphid (GPA) resistance to several organophosphate and carbamate insecticides is attributed to enhanced degradation of the insecticides by an E4 carboxylesterase, the product of amplified gene expression (Devonshire, A. L., et al., Pestic. Biochem. & Physiol. 18 235–246 (1982); Field et al., Biochem. J. 251 309–312 (1988); Moores et al, Pestic. Sci. 26 324–329 (1989)). Resistant GPA contain an E4 esterase content that is 2- to 64-fold higher than susceptible GPA (Devonshire & Sawicki, Nature 280 140–141 (1979)). O'Hara (M. S. Thesis, Michigan State University (1992)) found esterase-mediated resistance in GPA collected in Michigan and neighboring states, and the 1994 field studies suggest that this resistance is widespread throughout the major potato producing regions of Michigan.

The first component of each kit was six 11.0 cm filter papers (Waltman qualitative #1) treated with 1.0 ml of the esterase substrate, α-naphthyl acetate (1.2 mM), dissolved in acetone. These filter papers were wrapped in aluminum foil and sealed in a 15×22.5 cm clear resealable bag with a 6.0-g packet of moisture absorbent silica. The second component was a white plastic 15 ml eye-dropper bottle, with an attached snap lid, containing 10 ml of the color reagent, Diazo Blue (Fast Blue B salt) (2.4 mM), dissolved in distilled water. The kit procedure involved placing a treated filter paper onto a clipboard, knocking aphids from host plant onto the filter paper, covering aphids with a second filter paper, then crushing the aphids between filter papers. A small hand-held roller 20 (as shown in FIG. 1, Step 2) with a 10.0 cm wide, clear plastic cylinder was also used to crush aphids. After a 5 minute incubation period, the filter papers were separated and the number of resistant GPA (distinguished by a reddish-purple stain) are counted relative to the susceptible GPA (yellowish stain). Each insect produced a separate spot. The kits were found to be reliable in measuring insect resistance.

EXAMPLE 2

To test the sensitivity of the kit of Example 1 in distinguishing resistance from susceptible insects, brown planthopper, *Nilaparvata lugens*, was used from laboratory colonies selected for their susceptibility and resistance to organophosphate insecticides. The kit used as in Example 1 accurately distinguished between resistant and susceptible insects twenty-four (24) hours after kits were prepared. It was found that three (3) days later, the kit lost sensitivity and no longer detected resistant insects. This loss of sensitivity was apparently due to oxidation of the Diazo Blue in the aqueous solution. After two (2) months in storage at 4° C., the treated filter papers were effective in detecting resistant insects when fresh Diazo blue was used.

EXAMPLE 3

Dry Diazo blue was placed in the 1.5 ml bottles and water was added at the time of the test. This was done to avoid any oxidation of the Diazo Blue and to minimize handling of the dye reagent.

EXAMPLE 4

Several laboratory colonies of GPA with different susceptibilities to organophosphate insecticides were tested. The general esterase activity in each strain was tested with a microplate assay (Abdel-Aal, Y.A.I., et al, Pestic. Biochem. & Physiol. 38 255-266 (1990)); Bush, M. R., et al, J. Econ. Entomol. 86 213-225 (1993)) to compare activity levels with the results from the kits. This showed that the kits were accurate and sensitive to the esterases.

It is intended that the foregoing description be only illustrative of the present invention and that the present invention be limited only by the hereinafter appended claims.

We claim:

1. A method for detecting insect resistance to insecticides caused by an esterase produced by the insect which comprises:
    (a) providing an absorbent pad containing a dry substrate for the esterase which reacts to produce an intermediate compound and reacts with a chromogen to provide a visually detectable image;
    (b) crushing a single whole insect against the pad so that the esterase is released in the body fluid of the insect which reacts with the substrate to produce the intermediate compound;
    (c) removing the crushed insect from the absorbent pad;
    (d) reacting the intermediate compound in the absorbent pad containing the body fluid with the chromogen; and
    (e) determining an intensity of an image produced on the pad by the reaction of the esterase with the substrate and the intermediate compound with the chromogen, wherein the intensity of the image varies directly as a function of an amount of the esterase in the insect.

2. The method of claim 1 wherein the insect is an homopteran.

3. The method of claim 1 wherein the insect is a plant hopper.

4. The method of claim 1 wherein the insect is a homopteran and wherein the substrate is naphthyl acetate which reacts with the esterase to produce a naphthol as the intermediate compound which reacts with a dye as the chromogen to produce the visually detectable image on the pad.

5. The method of claim 4 wherein the dye is Fast Blue B salt.

6. The method of claim 5 wherein the insect is crushed on the pad using a roller.

7. The method of claim 1 wherein the pad is a filter paper impregnated with the substrate.

8. The method of claim 1 wherein the absorbent pad is mounted on a fluid impermeable sheet which is folded to crush the insect against the pad.

9. The method of claim 8 wherein the impermeable sheet contains an adhesive which removes the crushed insect from the absorbent pad.

10. A kit for detecting insect resistance to insecticides caused by an esterase produced by the insect which comprises:
    (a) an absorbent pad containing a dry substrate for the esterase which reacts with the enzyme to produce an intermediate compound which reacts with a chromogen to produce a visually detectable image on the pad;
    (b) press means for crushing the whole insect on the pad to release the esterase in body fluids of the insect which reacts with the substrate to produce the intermediate compound which reacts with the chromogen;
    (c) a dry chromogen which can be dissolved in water just prior to use, wherein an intensity of the image on the pad varies directly as a function of an amount of the esterase in the insect; and
    (d) means for removing the crushed insect from the absorbent pad.

11. The kit of claim 10 wherein the insect is crushed on the pad using a roller.

12. The kit of claim 10 wherein the pad is a filter paper impregnated with the substrate.

13. The kit of claim 10 wherein the insect is an homopteran aphid and wherein the substrate is naphthyl acetate which reacts with the esterase to produce naphthol as the intermediate compound which reacts with a dye as the chromogen to produce the visually detectable image on the pad.

14. The kit of claim 10 wherein the dye is Fast Blue B salt.

15. The test kit of claim 10 wherein the absorbent pad is mounted on a fluid impermeable sheet which can be folded to crush the insect against the pad.

16. The test kit of claim 15 wherein the impermeable sheet contains an adhesive which removes the crushed insect from the absorbent pad.

17. The test kit of claim 15 in a sealed container which is opened prior to use.

* * * * *